US00PP27397P2

(12) United States Plant Patent
Holtmaat

(10) Patent No.: US PP27,397 P2
(45) Date of Patent: Nov. 15, 2016

(54) ***HELENIUM* PLANT NAMED 'BANDERA'**

(50) Latin Name: *Helenium autumnale*
Varietal Denomination: Bandera

(71) Applicant: Henricus Maria Joseph Holtmaat, Zuidwolde (NL)

(72) Inventor: Henricus Maria Joseph Holtmaat, Zuidwolde (NL)

(73) Assignee: AB Kwekersrechten B.V., Zuidwolde (NL)

( * ) Notice: Subject to any disclaimer, the term of this patent is extended or adjusted under 35 U.S.C. 154(b) by 152 days.

(21) Appl. No.: 14/121,891

(22) Filed: Oct. 31, 2014

(51) Int. Cl.
*A01H 5/02* (2006.01)

(52) U.S. Cl.
USPC ..... Plt./435

(58) Field of Classification Search
USPC ..... Plt./435
See application file for complete search history.

*Primary Examiner* — Keith Robinson
(74) *Attorney, Agent, or Firm* — C. A. Whealy

(57) ABSTRACT

A new and distinct cultivar of *Helenium* plant named 'Bandera', characterized by its compact, broadly upright and uniformly mounding plant habit; moderately vigorous growth habit; freely flowering habit; inflorescences with dark yellow and dark orange bi-colored ray florets; and strong peduncles that hold the inflorescences above the foliar plane.

3 Drawing Sheets

Botanical designation: *Helenium autumnale.*
Cultivar denomination: 'BANDERA'.

BACKGROUND OF THE INVENTION

The present invention relates to a new and distinct cultivar of *Helenium* plant, botanically known as *Helenium autumnale* and hereinafter referred to by the name 'Bandera'.

The new *Helenium* plant is a product of a planned breeding program conducted by the Inventor in Zuidwolde, The Netherlands. The objective of the program is to create and develop new compact and freely-flowering *Helenium* plants with attractive ray and disc colors.

The new *Helenium* plant originated from an open-pollination in 2010 of an unidentified selection of *Helenium autumnale*, not patented, as the female, or seed, parent with an unknown selection of *Helenium autumnale* as the male, or pollen, parent. The new *Helenium* plant was discovered and selected by the Inventor as a single flowering plant within the progeny of the stated open-pollination in a controlled environment in Zuidwolde, The Netherlands in 2012.

Asexual reproduction of the new *Helenium* plant by terminal cuttings in a controlled greenhouse environment in Zuidwolde, The Netherlands since June, 2014 has shown that the unique features of this new *Helenium* plant are stable and reproduced true to type in successive generations.

SUMMARY OF THE INVENTION

Plants of the new *Helenium* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Bandera'.

These characteristics in combination distinguish 'Bandera' as a new and distinct *Helenium* plant:

1. Compact, broadly upright and uniformly mounding plant habit.
2. Moderately vigorous growth habit.
3. Freely flowering habit.
4. Inflorescences with dark yellow and dark orange bi-colored ray florets.
5. Strong peduncles that hold the inflorescences above the foliar plane.

In side-by-side comparisons conducted in Zuidwolde, The Netherlands, plants of the new *Helenium* differ from plants of the female parent selection primarily in plant habit as plants of the new *Helenium* are more uniformly mounding than plants of the female parent selection.

Plants of the new *Helenium* can be compared to plants of *Helenium hybrida* 'Fuego', disclosed in U.S. Plant Pat. No. 25,977. In side-by-side comparisons conducted in Zuidwolde, The Netherlands, plants of the new *Helenium* differed from plants of 'Fuego' in the following characteristics:

1. Plants of the new *Helenium* were more compact than plants of 'Fuego'.
2. Plants of the new *Helenium* and 'Fuego' differed slightly in ray floret color.

BRIEF DESCRIPTION OF THE PHOTOGRAPHS

The accompanying photographs illustrate the overall appearance of the new *Helenium* plant showing the colors as true as it is reasonably possible to obtain in colored reproductions of this type. Colors in the photographs may differ slightly from the color values cited in the detailed botanical description which accurately describe the colors of the new *Helenium* plant.

The photograph on the first sheet comprises a side perspective view of a typical flowering plant of 'Bandera' grown in a container.

The photograph on the second sheet is a close-up view of typical leaves of 'Bandera'.

The photograph on the third sheet is a close-up view of a typical flowering plant of 'Bandera'.

DETAILED BOTANICAL DESCRIPTION

The aforementioned photographs and following observations and measurements describe plants grown during the autumn in containers and ground beds in an outdoor nursery in Zuidwolde, The Netherlands and under cultural practices typical of commercial Helenium production. During the production of the plants, day temperatures ranged from 15° C. to 25° C. and night temperatures ranged from 3° C. to 15° C. Plants were two years old when the photographs and description were taken. In the following description, color references are made to The Royal Horticultural Society Colour Chart, 2007 Edition, except where general terms of ordinary dictionary significance are used.

Botanical classification: *Helenium autumnale* 'Bandera'.

Parentage:

*Female, or seed, parent*.—Unidentified selection of *Helenium autumnale*, not patented.

*Male, or pollen, parent*.—Unknown selection of *Helenium autumnale*, not patented.

Propagation:

*Type*.—Vegetative cuttings.

*Time to initiate roots, summer*.—About two weeks at temperatures about 20° C.

*Time to produce a rooted cutting, summer*.—About two months at temperatures about 20° C.

*Root description*.—Medium in thickness, fibrous.

*Rooting habit*.—Moderately freely branching; medium density.

Plant description:

*Plant and growth habit*.—Herbaceous perennial; compact, broadly upright and uniformly mounding plant habit; broad inverted triangle; freely basal branching with numerous flowering stems developing per plant; moderately vigorous growth habit.

*Plant height*.—About 47.5 cm.

*Plant width or area of spread*.—About 69.5 cm.

*Lateral branch description*.—Appearance: Mostly rounded with three axial "wings"; wings about 2 mm in width. Length: About 26.2 cm. Diameter: About 2.5 mm. Internode length: About 2.5 cm. Strength: Strong. Aspect: About 30° from vertical. Texture: Smooth, glabrous. Color: Close to 144B to 144C; wings, close to 143B.

Leaf description:

*Arrangement*.—Alternate; simple; sessile.

*Length*.—About 10.3 cm.

*Width*.—About 2.1 cm.

*Shape*.—Narrowly elliptic to oblanceolate.

*Apex*.—Acute.

*Base*.—Cuneate; decurrent.

*Margin*.—Shallowly serrate.

*Venation pattern*.—Pinnate.

*Texture, upper and lower surfaces*.—Smooth, glabrous.

*Color*.—Developing leaves, upper surface: Close to 143A to 143B. Developing leaves, lower surface: Close to 143C. Fully expanded leaves, upper surface: Close to N137A to N137B; venation, close to 144A. Fully expanded leaves, lower surface: Close to 137B to 137C; venation, close to 144A.

Inflorescence description:

*Appearance and arrangement*.—Single terminal inflorescences held above the foliar plane on strong erect peduncles; composite inflorescence form, radially symmetrical; obcordate to flabellate-shaped ray florets; disc florets massed at the center; ray and disc florets develop acropetally on a capitulum; inflorescences face mostly upright to outwardly.

*Natural flowering season*.—Plants begin flowering about nine months after planting; in outdoor nurseries and gardens in The Netherlands, plants flower continuous and freely from early August to early October.

*Postproduction longevity*.—Inflorescences maintain good color and substance for several weeks on the plant; inflorescences persistent.

*Quantity of inflorescences*.—Freely flowering habit; about 550 inflorescences developing per plant during the flowering season.

*Fragrance*.—None detected.

*Inflorescence buds*.—Length: About 8 mm. Diameter: About 2.4 cm. Shape: Flattened globular. Color: Close to 200B; immature ray florets, close to 166A and towards the apex, close to 154A.

*Inflorescence size*.—Overall diameter: About 4.5 cm. Depth (height): About 2.1 cm. Disc diameter: About 1.6 cm.

*Receptacles*.—Height: About 5 mm. Diameter: About 5 mm. Shape: Globular. Color: Close to 155A.

*Ray florets*.—Quantity and arrangement: About 16 ray florets arranged in a single whorl. Length: About 2 cm. Width: About 1.2 cm. Shape: Obcordate to flabellate; slightly concave. Apex: Three-lobed; lobe apices, obtuse. Base: Cuneate. Margin: Entire. Texture, upper surface: Smooth, glabrous; velvety; longitudinally ribbed. Texture, lower surface: Smooth, glabrous; longitudinally ribbed. Orientation: Initially upright then perpendicular to the peduncle. Color: When opening, upper surface: Close to 14B irregularly flushed and marbled with close to between 179A and N34A; towards the base, close to 9A. When opening, lower surface: Close to between 180A and N34A; towards the base, close to 9A. Fully opened, upper surface: Close to 13A irregularly flushed and marbled with close to between 178C to 178D and N34A; towards the base, close to 9A; with development, color becoming closer to 14B irregularly flushed and marbled with close to 180A and towards the base, close to 7A. Fully opened, lower surface: Close to 13A irregularly flushed and marbled with close to between 180A and N34A; towards the base, close to 9A; with development, color becoming closer to 14B irregularly flushed and marbled with close to 180A and towards the base, close to 7A.

*Disc florets*.—Quantity and arrangement: Numerous, about 320 disc florets arranged spirally at the center of the receptacle. Length: About 6 mm. Width: About 1.5 mm. Shape: Tubular, elongated; upper 20% of disc florets are free. Apex: Acute. Texture, inner and outer surfaces: Smooth, glabrous. Color, inner and outer surfaces, immature: Towards the apex, close to 200A; mid-section, close to 163C; towards the base, close to 145C to 145D. Color, inner and outer surfaces, mature: Towards the apex, close to 200A; mid-section, close to 163C; towards the base, close to 145C to 145D.

*Phyllaries*.—Quantity and arrangement: About 24 phyllaries arranged in a single whorl. Length: About 1.3 cm. Diameter: About 1 mm. Shape: Lanceolate. Apex: Narrowly acute. Base: Cuneate. Margin: Entire. Texture, upper and lower surfaces: Smooth, glabrous. Color, upper and lower surfaces: Close to 144A; towards the apex, close to 146B.

*Peduncles*.—Length, terminal peduncle: About 6.4 cm. Length, fourth peduncle: About 6.4 cm. Diameter: About 1.5 mm. Angle: Erect to about 20° from vertical. Strength: Strong. Texture: Moderately pubescent. Color: Close to 143B.

*Reproductive organs*.—Androecium: Present on disc florets only. Stamen number: Five per floret. Filament length: About 2 mm. Filament color: Close to 8A. Anther shape: Lanceolate. Anther length: About 2 mm. Anther color: Close to 12A. Pollen amount: Scarce. Pollen color: Close to 9A. Gynoecium: Present on both ray and disc florets. Pistil number: One per floret. Pistil length: About 3.75 mm. Stigma shape: Decurrent. Stigma color: Close to 13A. Style length: About 3 mm. Style color: Close to 12B. Ovary color: Close to 145D.

*Fruits and seeds*.—Fruit and seed development have not been observed on plant of the new *Helenium*.

Disease & pest resistance: Resistance to pathogens and pests common to *Helenium* plants has not been observed on plants grown under outdoor conditions.

Garden performance: Plants of the new *Helenium* have been observed to have good garden performance and to tolerate rain, wind, high temperatures about 35° C. and to be hardy to USDA Hardiness Zone 5.

It is claimed:

1. A new and distinct *Helenium* plant named 'Bandera' as illustrated and described.

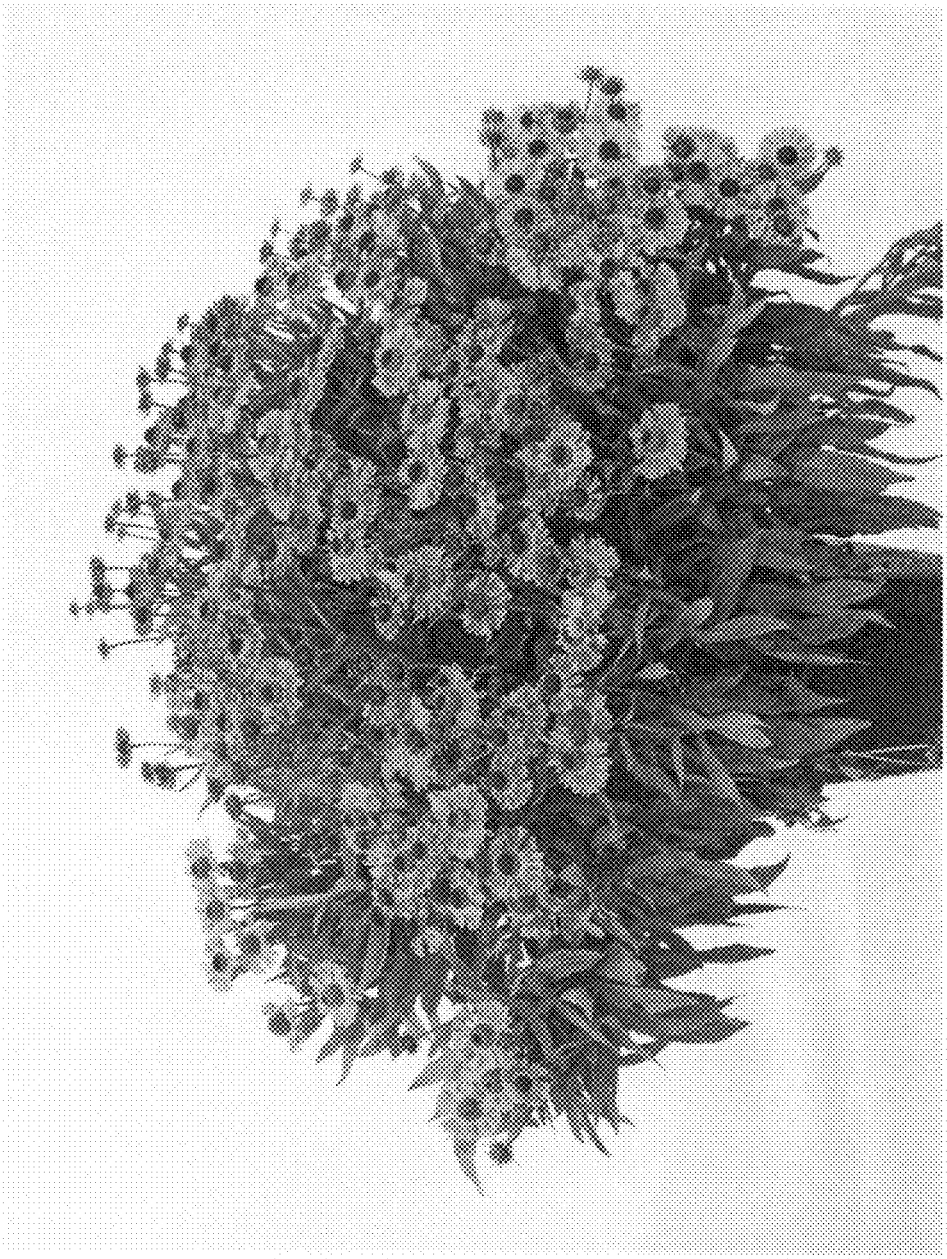

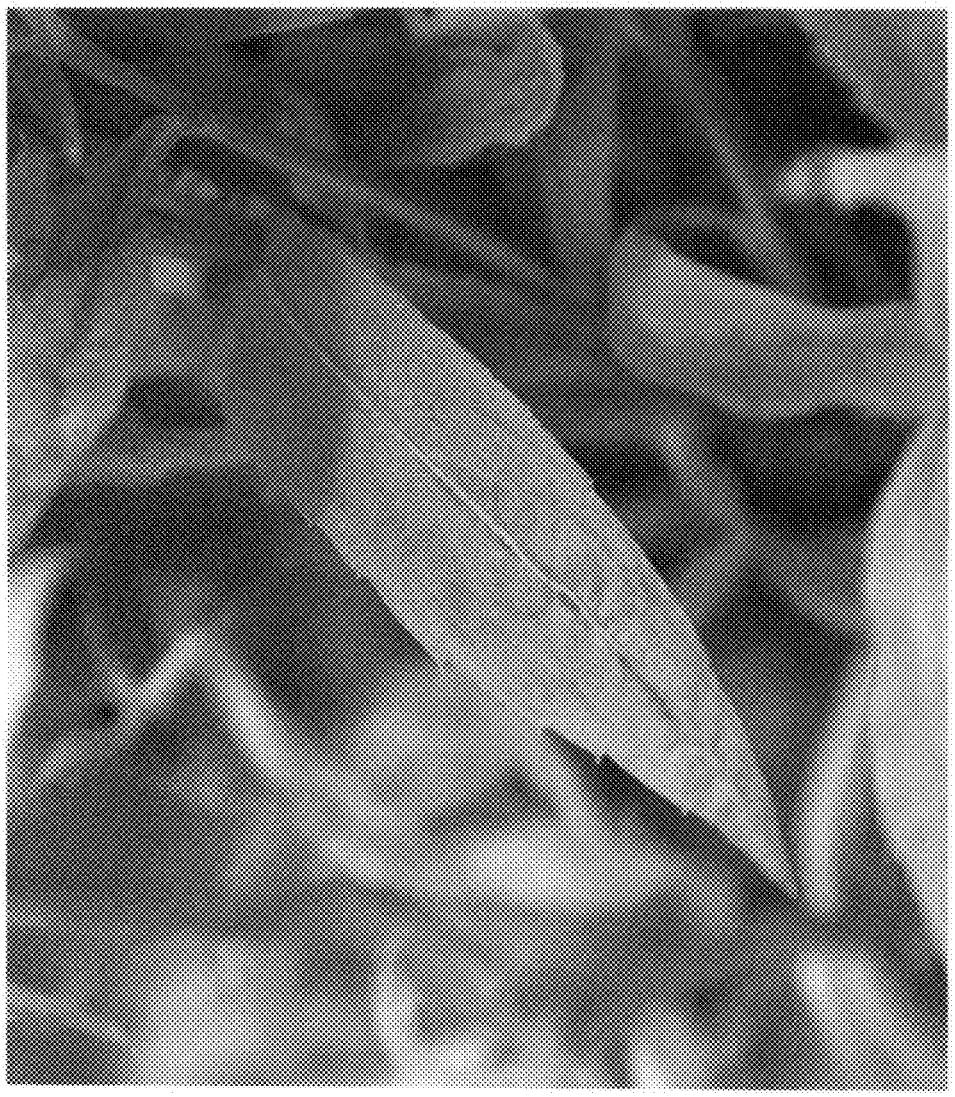

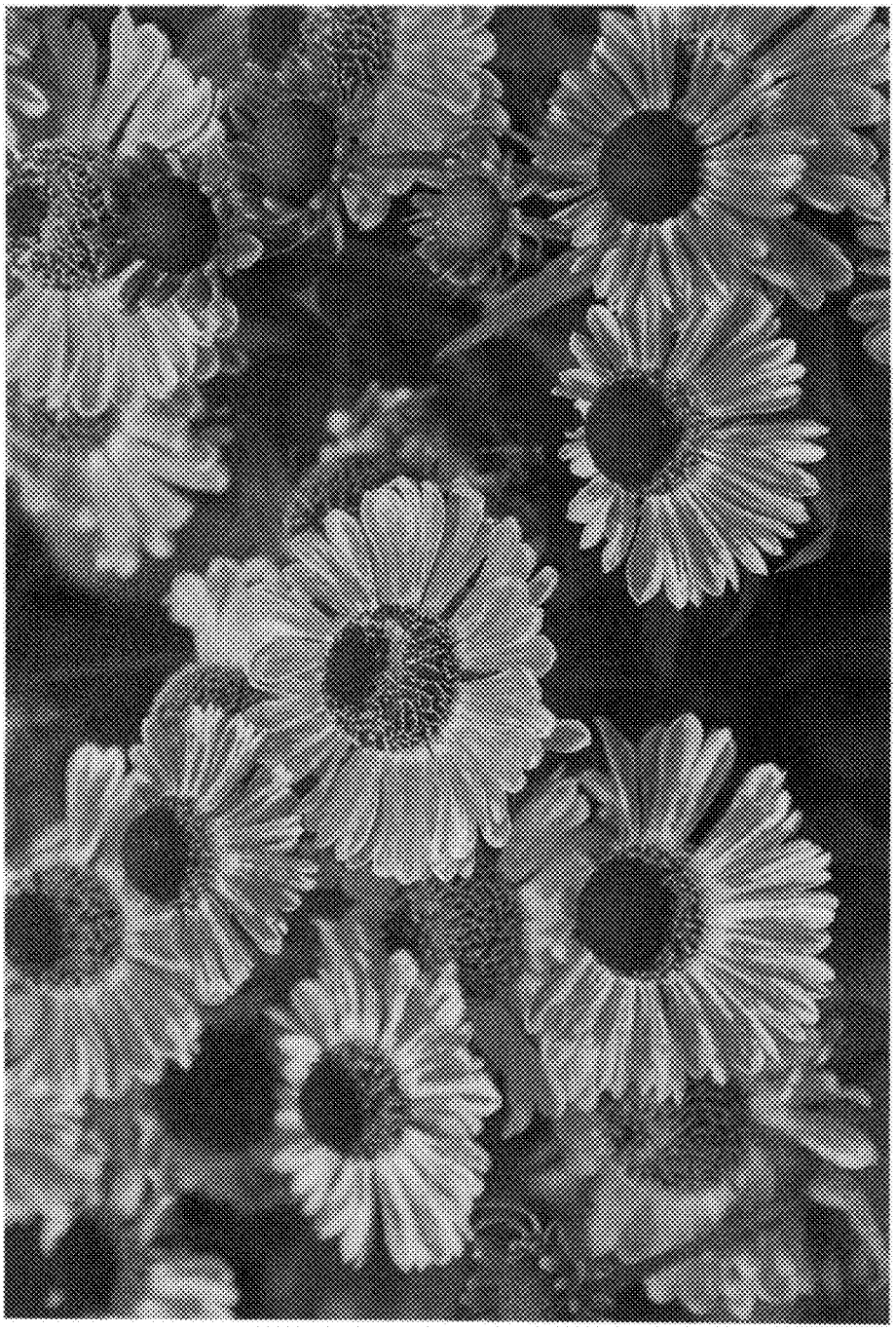

* * * * *